United States Patent [19]

Jeffries, III

[11] Patent Number: 5,346,808
[45] Date of Patent: Sep. 13, 1994

[54] POSITIVE IMAGE FORMATION UTILIZING O-QUINONEDIAZIDE COMPOSITION INCLUDING SELECTED PHENOLIC DERIVATIVES OF 4-(4-HYDROXYPHENYL)-CYCLOHEXANONE

[75] Inventor: Alfred T. Jeffries, III, Providence, R.I.

[73] Assignee: OCG Microelectronic Materials, Inc., West Paterson, N.J.

[21] Appl. No.: 148,235

[22] Filed: Nov. 8, 1993

Related U.S. Application Data

[62] Division of Ser. No. 45,024, Apr. 5, 1993, Pat. No. 5,283,374.

[51] Int. Cl.$^5$ .............................. G03F 7/32
[52] U.S. Cl. .................... 430/296; 430/326; 430/331; 430/942
[58] Field of Search ............... 430/191, 325, 326, 331, 430/296, 942

[56] References Cited

U.S. PATENT DOCUMENTS

| | | | |
|---|---|---|---|
| 5,010,163 | 4/1991 | Serini et al. | 528/204 |
| 5,112,719 | 5/1992 | Yamada et al. | 430/193 |
| 5,278,021 | 1/1994 | Jeffries, III et al. | 430/165 |
| 5,283,374 | 2/1994 | Jeffries, III | 568/721 |

FOREIGN PATENT DOCUMENTS

| | | |
|---|---|---|
| 1112980 | 8/1961 | Fed. Rep. of Germany . |
| 3291250 | 12/1991 | Japan . |
| 4012356 | 1/1992 | Japan . |
| 1252328 | 11/1971 | United Kingdom . |

*Primary Examiner*—Charles L. Bowers, Jr.
*Assistant Examiner*—Christopher G. Young
*Attorney, Agent, or Firm*—William A. Simons

[57] ABSTRACT

A radiation-sensitive composition comprising an admixture in a solvent of: at least one alkali-soluble binder resin, at least one photoactive compound and an effective sensitivity enhancing amount of at least one compound of formula (I):

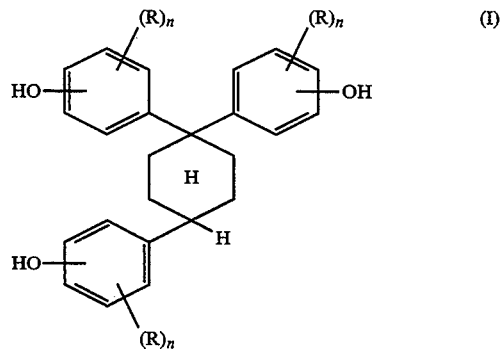

wherein each R is individually selected from the group consisting of hydrogen and a lower alkyl group having 1-4 carbon atoms and each n is 0, 1, or 2; the amount of said binder resin being about 60 to 95% by weight, the amount of said photoactive component being about 5% to about 40% by weight, based on the total solids content of said radiation-sensitive composition.

7 Claims, No Drawings

POSITIVE IMAGE FORMATION UTILIZING O-QUINONEDIAZIDE COMPOSITION INCLUDING SELECTED PHENOLIC DERIVATIVES OF 4-(4-HYDROXYPHENYL)-CYCLOHEXANONE

This application is a division of application Ser. No. 08/045,024 filed Apr. 5, 1993 now U.S. Pat. No. 5,283,370 which is incorporated herein by reference in its entirety.

BACKGROUND OF THE INVENTION

1. Field of the Invention

The present invention relates to radiation sensitive mixtures (e.g., those particularly useful as positive-working resist compositions) containing the admixture of an alkali-soluble binder resin, a photoactive compound and an effective sensitivity enhancing amount of at least one selected phenolic derivative of 4-(4-hydroxyphenol)cyclohexanone all dissolved in a solvent. Furthermore, the present invention also relates to substrates coated with these radiation sensitive mixtures as well as the process of coating, imaging and developing these radiation sensitive mixtures on these substrates.

2. Brief Description of Prior Art Including Information Disclosure Under 37 CFR § 1.97–1.99

Photoresist compositions are used in microlithographic processes for making miniaturized electronic components such as in the fabrication of integrated circuits and printed wiring board circuitry. In these processes, a thin coating or film of a photoresist composition is generally first applied to a substrate material, such as silicon wafers used for making integrated circuits or aluminum or copper plates of printed wiring boards. The preferred method of applying this film is spin coating. By this method, much of the solvent in the photoresist formulation is removed by the spinning operation. The coated substrate is then baked to evaporate any remaining solvent in the photoresist composition and to fix the coating onto the substrate. The baked coated surface of the substrate is next subjected to an image-wise exposure of radiation. This radiation exposure causes a chemical transformation in the exposed areas of the coated surface. Visible light, ultraviolet (UV) light, electron beam, ion beam, and X-ray radiant energy are radiation types commonly used today in microlithographic processes.

After this image-wise exposure, the coated substrate is treated with a developer solution to dissolve and remove either the radiation-exposed or the unexposed areas of the coated surface of the substrate. In some processes, it is desirable to bake the imaged resist coating before this developing step. This intermediate step is sometimes called post-exposure bake or PEB.

There are two types of photoresist compositions—negative-working and positive-working. When negative-working photoresist compositions are exposed image-wise to radiation, the areas of the resist composition exposed to the radiation become less soluble to a developer solution (e.g., a cross-linking reaction occurs) while the unexposed areas of the photoresist coating remain relatively soluble to a developing solution. Thus, treatment of an exposed negative-working resist with a developer solution causes removal of the nonexposed areas of the resist coating and the creation of a negative image in the photoresist coating, and thereby uncovering a desired portion of the underlying substrate surface on which the photoresist composition was deposited but not exposed to the radiation. On the other hand, when positive-working photoresist compositions are exposed image-wise to radiation, those areas of the resist composition exposed to the radiation become more soluble to the developer solution (e.g., the Wolff rearrangement reaction of the photoactive compound occurs) while those areas not exposed remain relatively insoluble to the developer solution. Thus, treatment of an exposed positive-working resist with the developer solution causes removal of the exposed areas of the resist coating and the creation of a positive image in the photoresist coating. The desired portion of the underlying substrate surface is uncovered where the photoresist was exposed to the radiation.

Positive-working photoresist compositions are currently favored over negative-working resists because the former generally have better resolution capabilities and pattern transfer characteristics.

After this development operation, the now partially unprotected substrate may be treated with a substrate-etchant solution or plasma gases and the like. This etchant solution or plasma gases etch the portion of the substrate where the photoresist coating was removed during development. The areas of the substrate are protected where the photoresist coating still remains and, thus, an etched pattern is created in the substrate material which corresponds to the photomask used for the image-wise exposure of the radiation. Later, the remaining areas of the photoresist coating may be removed during a stripping operation, leaving a clean etched substrate surface. In some instances, it is desirable to heat treat the remaining resist layer after the development step and before the etching step to increase its adhesion to the underlying substrate and its resistance to etching solutions.

End users of photoresists are demanding photoresist formulations possess better lithographic properties for the fabrication of smaller micro-electronic circuits. The lithographic properties which are critical to positive-working photoresist end-users include the following: (1) resolution capabilities in the submicron range without incomplete development in the exposed areas (i.e., scumming); (2) higher thermal image deformation temperatures (e.g., above 120° C.); (3) relatively fast photospeeds; (4) good adhesion to substrate; (5) good developer dissolution rates; (6) wide process latitude; (7) near to absolute vertical profiles (or good contrast) between exposed and unexposed photoresist areas after development; (8) good resistance to etching solutions and plasma etching techniques; (9) reduced tendency to form particulates; (10) mask linearity; and (11) low metal contamination.

Generally in the past, efforts to improve one of these lithographic properties have caused significant decreases in one or more of the other lithographic properties of the photoresist. Accordingly, there is a need for improved photoresist formulations which possess all of these desired properties without making significant tradeoffs. The present invention is believed to be an answer to that need.

For example, it is well known to add sensitivity enhancers (also known as photospeed enhancers or speed enhancers or dissolution rate enhancers) to resist formulations to increase the solubility of the resist coating in both the exposed and unexposed areas when the speed of development is an important processing consideration. However, some degree of contrast may be sacrificed with the addition of such sensitivity enhancers, (e.g., in positive-working resists, while the exposed areas of the resist coating will be more quickly developed, the sensitivity enhancers will also cause a larger loss of the resist coating from the unexposed areas). Thus, if too much resist coating is removed from the unexposed areas of a positive-working resins, film defects such as pinholes may be introduced into the coating or subsequent plasma etching steps may cause unwanted breakthroughs in the unexposed areas. Accordingly, sensitivity enhancers should provide the desired increased speed of development without the significant loss of film integrity.

Numerous compounds have been proposed as sensitivity enhancers in resist compounds. See U.S. Pat. Nos. 3,661,582; 4,009,033; 4,036,644; 4,115,128; 4,275,139; 4,365,019; 4,650,745; and 4,738,915 for examples of known sensitivity enhancers. All of these U.S. patents are incorporated herein by reference in their entities. While their known sensitivity enhancers may be suitable for some resist formulations or for some particular end uses, there is a need for new sensitivity enhancers which have better sensitivity enhancement without significant film loss in other resist formulations or in other end uses, or are suitable in a certain combination of resist formulations or a combination of end uses to which the previously known sensitivity enhancers are not suitable. The present invention is believed to be an answer to this need.

It is also known that novolak resins which are comprised of polyalklyated monomers (xylenols) have dissolution rates in standard non-metal alkaline developers which are slower than comparable novolaks derived from o-, m-, and p-cresol. When such resins are incorporated into positive acting photoresists certain undesirable side effects result. Thus, increasing the developer strength or prolonging development times causes degradation of the resist image, and generally requires unacceptable process changes.

It has been found that selected polynuclear (poly)-monohdydric phenols, i.e., those which one or less hydroxyl group per nucleus are efficacious at enhancing the dissolution rate of such novolaks. Further, they have the desirable properties of reducing scum, increasing resolution and sidewall angle, among other things.

Separately, Japanese Patent Publication (Kokai) No. 3-291250, which was published on Dec. 20, 1991, teaches a phenolic compound defined by the structure of formula (PA-1):

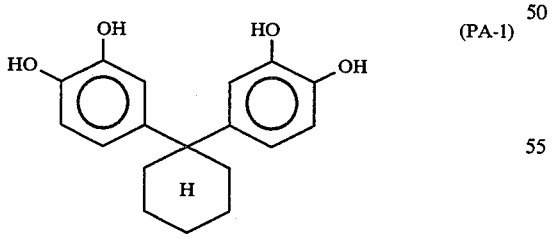

(PA-1)

This Kokai also teaches that positive photoresist compositions may be made which contain photoactive compounds made of the ester of compound (PA-1) with a quinonediazidesulfonate. The reference suggests that these photoresist compositions provide high gamma values without an increase in residues in development.

Also, Japanese Patent Publication (Kokai) No. 4-012356, which was published on Jan. 16, 1992, teaches a positive-working photoresist composition containing a novolak resin, a quinonediazide compound, and a polyhydric phenolic compound having the structure of formula (PA-2):

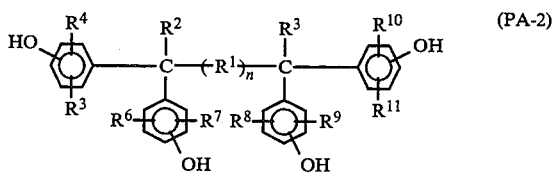

(PA-2)

wherein $R^1$ is a bifunctional hydrocarbon, n is 0 or 1, $R^2$ and $R^3$ are selected from hydrogen, alkyl, aryl, or aralkyl group; $R^2$ and $R^3$ are optionally combined to form a cyclic structure; $R^4$, $R^5$, $R^6$, $R^7$, $R^8$, $R^9$, $R^{10}$, and $R^{11}$ are selected from hydrogen, halogen, hydroxyl, or an alkyl group. This Kokai suggests that these positive photoresist compositions possess high photosensitivity and are useful for high density integrated circuit fabrication.

One polyhydric phenolic compound encompassed by the above formula is the following compound (PA-2a):

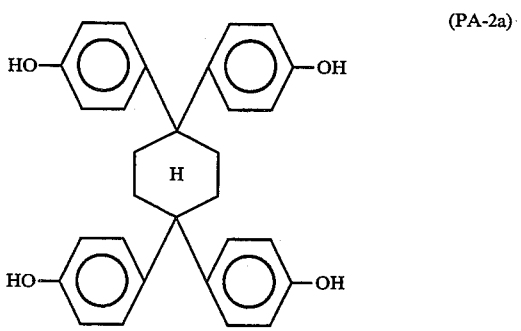

(PA-2a)

SUMMARY OF THE INVENTION

Accordingly, one aspect of the present invention is directed to polyhydric phenolic compounds, as compositions of matter, having the formula (I):

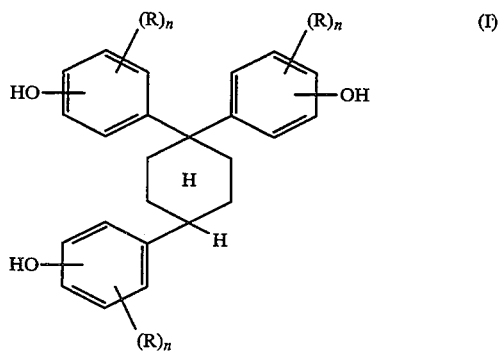

(I)

wherein each R is individually selected from the group consisting of hydrogen and a lower alkyl group having 1–4 carbon atoms and each n is 0, 1, or 2.

Another aspect of the present invention is directed to a radiation sensitive composition useful as a positive-working resist comprising an admixture in a solvent of:
(a) at least one photoactive compound;
(b) at least one alkali-soluble binder resin; and
(c) an effective sensitivity enhancing amount of at least one compound of above formula (I); the amount of said photoactive compound or compounds being about 5% to about 40% by weight and the amount of said binder resin or resins being about 60 to 95% by weight, based on the total solids content of said radiation sensitive mixture.

Furthermore, the present invention also encompasses the process of coating substrates with these radiation sensitive mixtures and their exposing and developing these coated substrates.

Also further, the present invention encompasses said coated substrates (both before and after imaging) as novel articles of manufacture.

DESCRIPTION OF THE PREFERRED EMBODIMENTS

As mentioned above, the radiation-sensitive compositions of the present invention have three critical ingredients; at least one alkali-soluble binder resin; at least one photoactive compound; and at least one polyhydric phenolic compound of formula (I).

Any or all binder resins commonly employed in photoresist compositions may be used herein. The preferred class of binder resins is alkali-soluble resin or resins which are useful in positive-working photoresist compositions. The term "alkali-soluble binder resin" is used herein to mean a resin which will dissolve completely in an aqueous alkaline developing solution conventionally used with positive-working photoresist compositions. Suitable alkali-soluble resins include phenolic novolaks such as phenol-formaldehyde novolak resins, cresol-formaldehyde novolak resins, or polyvinyl phenol resins, preferably those having an average molecular weight of about 500 to about 40,000, and more preferably from about 800 to 20,000. The novolak resins are preferably prepared by the condensation reaction of phenol or cresols with formaldehyde and are characterized by being light-stable, water-insoluble, alkali-soluble, and film-forming. The most preferred class of novolak resins is formed by the condensation reaction between a mixture of meta- and para-cresols with formaldehyde.

Any and all photoactive compounds which make radiation-sensitive mixtures useful as photoresists may be employed herein. The preferred class of photoactive compounds (sometimes called "sensitizers") is o-quinonediazide compounds, particularly esters derived from polyhydric phenols, alkyl-polyhydroxyphenones, aryl-polyhydroxyphenones, and the like which can contain up to six or more sites for esterification. The most preferred o-quinonediazide esters are derived from 3-diazo-3,4-dihydro-4-oxo-naphthalene-1-sulfonic acid chloride (also know as 1,2-naphthoquinonediazide-4-sulfonyl chloride) and 6-diazo-5,6-dihydro-5-oxo-naphthalene-1-sulfonic acid chloride (also known as 1,2-naphthoquinonediazide-5-sulfonyl chloride).

Specific examples include resorcinol 1,2-naphthoquinonediazide-4-sulfonic acid esters; pyrogallol 1,2-naphthoquinonediazide-5-sulfonic acid esters, 1,2-quinonediazidesulfonic acid esters of (poly)hydroxyphenyl alkyl ketones or (poly)hydroxyphenyl aryl ketones such as 2,4-dihydroxyphenyl propyl ketone 1,2-benzoquinonediazide-4-sulfonic acid esters, 2,4-dihydroxyphenyl hexy ketone 1,2-naphthoquinonediazide-4-sulfonic acid esters, 2,4-dihydroxybenzophenone 1,2-naphthoquinonediazide-5-sulfonic acid esters, 2,3,4-trihydroxyphenyl hexyl ketone, 1,2-naphthoquinonediazide-4-sulfonic acid esters, 2,3,4-trihydroxybenzophenone 1,2-naphthoquinonediazide-4-sulfonic acid esters, 2,3,4-trihydroxybenzophenone 1,2-naphthoquinonediazide-5-sulfonic acid esters, 2,4,6-trihydroxybenzophenone 1,2-naphthoquinonediazide-4-sulfonic acid esters, 2,4,6-trihydroxybenzophenone 1,2-naphthoquinone-diazide-5-sulfonic acid esters, 2,2',4,4'-tetrahydroxy-benzophenone 1,2-naphthoquinonediazide-5-sulfonic acid esters, 2,3,4,4'-tetrahydroxy-benzophenone, 1,2-naphthoquinonediazide-5-sulfonic acid esters, 2,3,4,4'-tetrahydroxybenzophenone 1,2-naphthoquinone-diazide-4-sulfonic acid esters, 2,2',3,4',6'-pentahydroxybenzophenone 1,2-naphthoquinone-diazide-5-sulfonic acid esters, and 2,3,3',4,4',5'-hexahydroxy-benzophenone 1,2-naphthoquinonediazide-5-sulfonic acid esters; 1,2-quinonediazidesulfonic acid esters of bis[(poly)-hydroxyphenyl]alkanes such as bis(p-hydroxypheny)methane 1,2-naphthoquinonediazide-4-sulfonic acid esters, bis(2,4-dihydroxyphenyl)methane 1,2-naphthoquinonediazide-5-sulfonic acid esters, bis(2,3,4-trihydroxyphenyl)methane 1,2-naphthoquinonediazide-5-sulfonic acid esters, 2,2-bis(p-hydroxyphenyl)propane 1,2-naphthoquinonediazide-4-sulfonic acid esters, 2,2-bis(2,4-dihydroxyphenyl)propane 1,2-naphthoquinonediazide-5-sulfonic acid esters and 2,2-bis(2,3,4-trihydroxyphenyl)propane 1,2-naphthoquinonediazide-5-sulfonic acid esters. Besides the 1,2-quinonediazide compounds exemplified above, there can also be used the 1,2-quinonediazide compounds described in J. Kosar, "Light-Sensitive Systems", 339–352 (1965), John Wiley & Sons (New York) or in S. DeForest, "Photoresist", 50, (1975), MacGraw-Hill, Inc. (New York). In addition, these materials may be used in combinations of two or more. Further, mixtures of substances formed when less than all esterification sites present on a particular polyhydric phenol, alkyl-polyhydroxyphenone, aryl-polyhydroxyphenone and the like have combined with o-quinoediazides may be effectively utilized in positive acting photoresists.

Of all the 1,2-quinonediazide compounds mentioned above, 1,2-naphthoquinonediazide-5-sulfonic acid di-, tri-, tetra-, penta-, and hexa-esters of polyhydroxy compounds having at least 2 hydroxyl groups, i.e., about 2 to 6 hydroxyl groups, are one class of preferred compounds.

Among this class of preferred 1,2-naphthoquinonediazide compounds are 2,3,4-trihydroxybenzophenone 1,2-naphthoquinone-diazide-5-sulfonic acid esters, 2,3,4,4'-tetrahydroxy-benzophenone 1,2-naphthoquinonediazide-5-sulfonic acid esters, and 2,2',4,4'-tetra-hydroxybenzo-phenone 1,2-naphthoquinonediazide-5-sulfonic acid esters. Another preferred 1,2-quinonediazide compound is mixed 1,2-naphthoquinonediazide-5-sulfonic acid esters of 2,2'3,3'-tetrahydro-3,3,3',3'-tetramethyl-1,1-spirobi (1H-indene)-5,5'6,6'7,7'-hexol (C.A.S. Reg. No. 32737-33-0). These 1,2-naphthoquinonediazide compounds may be used alone or in combination of two or more.

Another preferred 1,2-naphthoquinone-5-diazide compounds are phenol 1,2-naphthoquinonediazide-5-sulfonic acid ester and bis[4-(2,6-dimethylphenol)]-4-catehol methane 1,2-naphthoquinone-5-diazide sulfonic acid esters.

Another preferred class of photoactive o-quinonediazide compounds is prepared by condensing spirobiindane or spirobichroman derivatives with 1,2-naphthoquinonediazido-4-sulfonyl chloride or 1,2-naphthoquinonediazide-5-sulfonyl chloride or a mixture thereof to make compounds of formula (A) shown below:

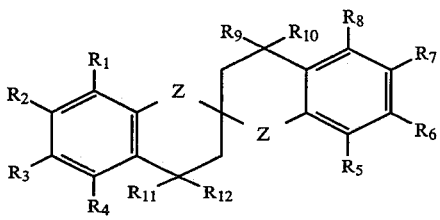 (A)

wherein $R_1$ to $R_8$ are independently hydrogen, a hydroxyl group, a halogen atom, an alkyl group, an alkoxy group, an aralkyl group, an aryl group, an amino group, a monoalkylamino group, a dialkylamino group, an acylamino group, an alkylcarbamoyl group, an arylcarbamoyl group, an alkylsulfamoyl group, an arylsulfamoyl group, a carboxyl group, a cyano group, a nitro group, an acyl group, an alkyloxycarbonyl group, an aryloxycarbonyl group, an acyloxy group,

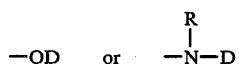

(wherein R is hydrogen, or an alkyl group, and D is a 1,2-naphthoquinonediazido-5-sulfonyl group or a 1,2-naphthoquinonediazido-4-sulfonyl group); $R_9$ to $R_{12}$ are independently hydrogen or a lower alkyl group; and Z is oxygen or a single bond (i.e. the latter forms a five-member ring); provided that at least one of $R_1$ to $R_8$ is

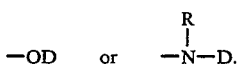

The halogen represented by $R_1$ to $R_8$ in the formula (A) is preferably chlorine, bromine or iodine.

The alkyl group is preferably an alkyl group having 1 to 4 carbon atoms, such as methyl, ethyl, propyl, isopropyl, n-butyl, isobutyl, sec-butyl and tert-butyl.

The alkoxy group is preferably an alkoxy group having 1 to 4 carbon atoms, such as methoxy, ethoxy, hydroxyethoxy, propoxy, hydroxypropoxy, isopropoxy, n-butoxy, isobutoxy, sec-butoxy and tert-butoxy.

The aralkyl group is preferably a benzyl group, a phenethyl group or a benzhydryl group.

The aryl group is preferably phenyl, tolyl, hydroxyphenyl or naphthyl.

The monoalkylamino group is preferably a monoalkylamino group having 1 to 4 carbon atoms, such as monomethylamino, monoethylamino, mono-propylamino, monoisopropylamino, mono-n-butylamino, monoisobutylamino, mono-sec-butylamino, or mono-tert-butylamino.

The dialkylamino group is preferably a dialkylamino group with each alkyl substituent having 1 to 4 carbon atoms, such as dimethylamino, diethylamino, di-propylamino, di-isopropylamino, di-n-butylamino, di-iso-butylamino, di-sec-butylamino, or di-tert-butylamino.

The acylamino group is preferably an aliphatic group-substituted acylamino group such as acetylamino, propionylamino, butylamino, isobutylamino, isovalerylamino, pivaloylamino or valerylamino, or an aromatic group-substituted acylamino group such as benzoylamino or toluoylamino.

The alkylcarbamoyl group is preferably an alkylcarbamoyl group having 2 to 5 carbon atoms, such as methylcarbamoyl, n-ethylcarbamoyl, propylcarbamoyl, isopropylcarbamoyl, n-butylcarbamoyl, isobutylcarbamoyl, sec-butylcarbamoyl, or tert-butylcarbamoyl.

The arylcarbamoyl group is preferably phenylcarbamoyl or tolylcarbamoyl.

The alkylsulfamoyl group is preferably an alkylsulfamoyl group having 1 to 4 carbon atoms, such as methylsulfamoyl, ethylsulfamoyl, propylsulfamoyl, isopropylsulfamoyl, n-butylsulfamoyl, sec-butylsulfamoyl, or tert-butylsulfamoyl.

The arylsulfamoyl group is preferably phenylsulfamoyl or tolylsulfamoyl.

The acyl group is preferably an aliphatic acyl group having 1 to 5 carbon atoms, such as formyl, acetyl, propionyl, butyryl, isobutyryl, valeryl, isovaleryl or pivaloyl, or an aromatic acyl group, such as benzoyl, toluoyl, salicyloyl, or naphthoyl.

The alkyloxycarbonyl group is preferably an alkyloxycarbonyl group having 2 to 5 carbon atoms, such as methoxycarbonyl, ethoxycarbonyl, propoxycarbonyl, isopropoxycarbonyl, n-butoxycarbonyl, isobutoxycarbonyl, sec-butoxycarbonyl, or tert-butoxycarbonyl.

The aryloxycarbonyl group is preferably phenoxycarbonyl.

The acyloxy group is preferably an aliphatic acyloxy group having 2 to 5 carbon atoms, such as acetoxy, propionyloxy, butyryloxy, isobutyryloxy, valeryloxy, isovaleryloxy or pivaloyloxy, or an aromatic acyloxy group such as benzoyloxy, toluoyloxy, or naphthoyloxy.

The lower alkyl group represented by $R_9$ to $R_{12}$ in the formula (A) is preferably an alkyl group having 1 to 4 carbon atoms, such as methyl, ethyl, propyl, isopropyl, butyl, isobutyl, sec-butyl, or tert-butyl.

In the formula (A) above, $R_1$ to $R_8$ are preferably a hydrogen atom, a hydroxy group or an —OD group wherein D is as defined above, and $R_9$ to $R_{12}$ are preferably a hydrogen atom or a methyl group. R is preferably an alkyl group having 1 to 4 carbon atoms, such as a methyl, ethyl, n-propyl, isopropyl, n-butyl, isobutyl, sec-butyl, or t-butyl group.

The proportion of the photoactive compound in the radiation-sensitive mixture may range from about 5% to about 40%, more preferably from about 10% to about 25% by weight of the nonvolatile (e.g., nonsolvent) content of the radiation-sensitive mixture. The proportion of total binder resin of this present invention in the radiation-sensitive mixture may range from about 60% to about 95%, preferably, from about 75% to 90% by weight, of the nonvolatile (e.g., excluding solvents) content of the radiation-sensitive mixture.

The third critical ingredient of the present invention is phenolic derivative of 4-(4-hydroxyphenol)cyclohexanone. The most preferred phenolic derivative of 4-(4-hydroxyphenol)cyclohexanone is 1,1,4-tris(4-hydroxyphenyl)cyclohexane.

The term "effective sensitivity enhancing amount" as used herein means any amount of the phenolic derivative of 4-(4-hydroxyphenyl)cyclohexanone compound or compounds which will increase the sensitivity of the radiation-sensitive mixture.

The preferred proportion of the phenolic derivative of 4-(4-hydroxyphenyl)cyclohexanone compound or compounds in the radiation-sensitive mixture may range from about 0.5% to about 10%, preferably about 2 to 4% by weight of nonvolatile (e.g., excluding solvents) content of the radiation-sensitive mixture.

These radiation-sensitive mixtures may also contain, besides the resin, photoactive compound and the polyhydric phenolic compound of formula (I), conventional photoresist composition ingredients such as other resins, solvents, actinic and contrast dyes, anti-striation agents, plasticizers, other sensitivity enhancers, and the like. These additional ingredients may be added to the binder resin, photoactive compound and polylactide compound solution before the solution is coated onto the substrate.

The binder resin, photoactive compound or sensitizer, and the polyhydric phenolic compound of formula (I) may be dissolved in a solvent or solvents to facilitate their application to the substrate. Examples of suitable solvents include methoxyacetoxy propane, diglyme, toluene, ethyl cellosolve acetate, n-butyl acetate, ethyl lactate, propylene glycol alkyl ether acetates, or mixtures thereof and the like. Cosolvents such as xylene, n-butylacetate, or ethyl ethoxy propionate or the like may also be used. The most preferred solvent is ethyl lactate alone or in combination with another solvent (e.g., ethyl 3-ethoxy propionate). The preferred amount of solvent may be from about 50% to about 500%, or higher, by weight, more preferably, from about 100% to about 400% by weight, based on combined resin, sensitizer, and dimeric or trimeric unit weight.

Actinic dyes help provide increased resolution on highly reflective surfaces by inhibiting back scattering of light off the substrate. This back scattering causes the undesirable effect of optical notching, especially on a substrate topography. Examples of actinic dyes include those that absorb light energy at approximately 400–460 nm [e.g., Fat Brown B (C.I. No. 12010); Fat Brown RR (C.I. No. 11285); 2-hydroxy-1,4-naphthoquinone (C.I. No. 75480) and Quinoline Yellow A (C.I. No. 47000) and Macrolex Fluoroyellow 10 GN (C.I. No. Solvent Yellow 16:1)] and those that absorb light energy at approximately 300–340 nm [e.g. 2,5-diphenyloxazole (PPO-Chem. Abs. Reg. No. 92-71-7) and 2-(4-biphenyl)-6-phenyl-benzoxazole (PBBO-Chem. Abs. Reg. No. 17064-47-0)]. The amount of actinic dyes may be up to 10% weight levels, based on the combined weight of resin and sensitizer.

Contrast dyes enhance the visibility of the developed images and facilitate pattern alignment during manufacturing. Examples of contrast dye additives that may be used together with the radiation-sensitive mixtures of the present invention include Solvent Red 24 (C.I. No. 26105), Basic Fuchsin (C.I. 42514), Oil Blue N (C.I. No. 61555) and Calco Red A (C.I. No. 26125) up to 10% weight levels, based on the combined weight of resin and sensitizer.

Anti-striation agents or leveling agents level out the resist coating or film to a uniform thickness. In other words, the leveling agent is used to eliminate the formation of striations on the surface of the resist coating once the coating is spun onto the substrate surface. Anti-striation agents may be used up to 5% weight levels, based on the weight of solids in the resist formulation. One suitable class of anti-striation agents is nonionic silicon-modified polymers. A preferred one is TROYKYD 366 made by Troy Chemical Co., Newark, N.J. Another suitable class of anti-striation agents is fluoroaliphatic polymeric ester surfactants. A preferred one is FC-430 FLUORAD made by 3M of St. Paul, Minn. Nonionic surfactants may also be used for this purpose, including, for example nonylphenoxy poly(ethyleneoxy) ethanol; octylphenoxy (ethyleneoxy) ethanol; and dinonyl phenoxy poly(ethyleneoxy) ethanol; polyoxyethylene lauryl ether; polyoxyethylene oleyl ether; polyoxyethylene octylphenyl ether; polyoxyethylene nonylphenyl ether; polyoxyethylene glycol dilaurate; and polyoxyethylene glycol distearate. Also may be useful are orgnosiloxane polymers and acrylic acid-containing or methacrylate acid-containing polymers.

The photoresist coatings produced by the above described procedure are particularly suitable for application to silicon/silicon dioxide-coated or polysilicon or silicon nitride wafers such as are utilized in the production of microprocessors and other miniaturized integrated circuit components. An aluminum/aluminum oxide wafer can be used as well. The substrate may also comprise various polymeric resins especially transparent polymers such as polyesters and polyolefins.

After the resist solution is coated onto the substrate, the coated substrate may be preferably baked at approximately 70° to 125° C. until substantially all the solvent has evaporated and only a uniform radiation-sensitive coating remains on the substrate.

The coated substrate can then be exposed to radiation, in any desired exposure pattern, produced by use of suitable masks, negatives, stencils, templates, and the like. Conventional imaging process or apparatus currently used in processing photoresist-coated substrates may be employed with the present invention. While ultraviolet (UV) light and electron beam radiations are the preferred sources of radiation, other sources such as visible light, ion beam, and X-ray radiant energy may be instead used. In some instances, a post-exposure bake at a temperature about 10° C. higher than the soft bake temperature for about 30–300 seconds is used to enhance image quality and resolution.

The exposed resist-coated substrates are next developed in an aqueous alkaline solution. This solution is preferably agitated, for example, by nitrogen gas. Examples of aqueous alkaline developers include aqueous solutions of tetramethylammonium hydroxide, sodium hydroxide, potassium hydroxide, ethanolamine, choline, sodium phosphates, sodium carbonate, sodium metasilicate, and the like. The preferred developers for this invention are aqueous solutions of either alkali metal hydroxides, phosphates or silicates, or mixtures thereof, or tetramethylammonium hydroxide.

Alternative development techniques such as spray development or puddle development, or combinations thereof, may also be used.

The substrates are allowed to remain in the developer until all of the resist coating has dissolved from the exposed areas. Normally, development times from about 10 seconds to about 3 minutes are employed.

After selective dissolution of the coated wafers in the developing solution, they are preferably subjected to a deionized water rinse to fully remove the developer or any remaining undesired portions of the coating and to stop further development. This rinsing operation (which is part of the development process) may be followed by blow drying with filtered air to remove excess water. A post-development heat treatment or bake may then be employed to increase the coating's adhesion and chemical resistance to etching solutions and other substances. The post-development heat treatment can comprise the baking of the coating and substrate below the coating's thermal deformation temperature.

In the manufacture of microcircuitry units, the developed substrates may then be treated with a plasma gas etch employing conventional plasma processing parameters (e.g., pressure and gas flow rates) and conventional plasma equipment.

Later, the remaining areas of the photoresist coating may be removed from the etched substrate surface by conventional photoresist stripping operations.

The present invention is further described in detail by means of the following Examples. All parts and percentages are by weight unless explicitly stated otherwise.

EXAMPLE 1

Preparation of 1,1,4-tris(4-hydroxyphenyl)cyclohexane

The reaction was conducted in a 500 mL three-neck flask fitted with a mechanical stirring apparatus, Friedrichs condenser, and a gas inlet tube. the gas inlet tube was connected to a lecture bottle of hydrogen chloride gas through rubber tubing and a suction trap. The reaction mixture's temperature was controlled by an oil bath connected to a programmable temperature controller (Ace Glass Catalog No. 12115-09).

To the flask was added 4-(4-hydroxyphenyl)cyclohexanone (40.0 g, 0.210 mole) and phenol (158.5 g, 1.68 mole). The flask and contents were added to the oil bath whose temperature was at 30° C. Stirring was begun and the HCl gas was bubbled slowly into the mixture below the surface.

The reaction mixture's temperature was controlled according to the following program: 30° C., 30 minutes, increase the temperature to 50° C. over 30 minutes from 30° C. 50° C. for 3.5 hours. The HCl gas was bubbled through the mixture slowly for the first two steps and intermittently during the 3.5 hour reaction period. The contents of the flask become a paste during reaction.

After heating, the thick paste was diluted with 450 mL toluene, cooled in an ice/water bath and isolated by filtration. It was treated with portions of toluene and methylene chloride until the amount of residual phenol was less than 1 area percent by HPLC analysis. The solid was isolated by filtration and was 90% pure by HPLC analysis, product weight, 57.7 g (76%).

EXAMPLE 2

Dissolution Rate Measurement

In order to measure the ability of a substance to increase the dissolution rate of a given novolak, the dissolution rate of a standard novolak film and that of the same novolak plus the speed enhancer of Example 1 were compared. The time to clear is that time required to a one micron novolak film coated and baked on a 4 inch (10 centimeter) silicon wafer to completely dissolve in an aqueous tetramethylammonium hydroxide (TMAH) solution.

The standard novolak film was made by first dissolving a standard phenolic novolak into a 70/30 weight:weight ethyl lactate and ethyl 3-ethoxy propionate solvent mixture. A second solution was made by combining the triphenol of Example 1, 1.54 g, with 28.46 g of the same novolak in the same 70/30 weight:weight ethyl lactate and ethyl 3-ethoxy propionate solved mixture. The solutions were filtered through an 0.2 micron filter. The solutions were both spin coated by pouring about 3 mL of each solution onto 4" silicon wafers. The solutions were spread at 500 RPM and finally at 3,000–6,000 RPM to give films on the wafers. The films were baked on a vacuum chuck hot plate at 115° C. for 60 seconds. Film thickness was determined using a Prometric SM200E profilometer and a Gaertner elipsometer. The coated wafers were placed in a 0.262N TMAH solution with good agitation and the time for the film to completely dissolve was recorded as the time to clear.

The time to clear of the standard novolak was 329 sec. and that of the novolak plus speed enhancer was 29.4 sec.

EXAMPLE 3

Resist Formulation with Speed Enhancer, 19% PAC

A solution of STN novolak (50.0 g at 30% solids in methyl-3-methoxypropionate) with a time to clear of about 250 sec/micron in 0.262 aqueous tetramethylammonium hydroxide was mixed with 3.07 g of the product produced in Example 1. A mixture of photoactive compounds (PACS) consisting of 3.00 g of 4-TPM and 1.30 g of 3-TPM PAC was dissolved in the novolak solution. Additionally 0.0539 g of F-8 dye and 0.25 g of FC-430 leveling agent were added to the solution. Further, 25.01 g of methyl-3-methoxypropionate was added to the solution to complete the formulation. The resist solution was filtered through an 0.2 micron filter.

The STN novolak was prepared by condensing a mixture of substituted phenols with formaldehyde according to general procedure set forth in U.S. patent application Ser. No. 07/713,891 filed by Charles E. Ebersole on Jun. 19, 1991. The phenolic composition of this novolak is 20% p-cresol (as dimers), 50% 2,3-dimethyphenol, 20% 2,3,5-trimethylphenol, 8% 2,6-dimethylphenol, and 2% o-cresol. The 3-TPM PAC is the product of esterifying about 2.6 moles of 2,1-diazonaphthoquinone-5-sulfonyl chloride (DNQ) with one mole of bis-[3,5-dimethyl-4-hydroxyphenyl]3-methoxy-4-hydroxyphenyl methane. The 4-TPM PAC is the product of esterifying about 2.3 moles of DNQ with one mole of bis-[3,5-dimethyl-4-hydroxyphenyl]-3,4-dihydroxyphenyl methane. The F-8 dye is 2-hydroxy-4-dibutylamine-2'-carboxybenzophenone. The FC-430 leveling agent is a fluoroaliphatic polymeric ester surfactant.

RESIST PROCESSING: A resist coating from Example 3 was prepared by spin coating on 100 millimeter diameter silicon wafer and soft baked at 90° C. for one minute. Coated wafer was exposed to patterned ultraviolet radiation at 365 nm using a step and repeat Canon 0.52 exposure unit. Exposed waters were then baked for one minute at 120° C. and developed in puddle mode for one minute using an aqueous alkaline solution of 0.262N TMAH.

RESULTS: The relative resist photospeed (Eo) for the resist prepared according to Example 3 was 150 mJ/cm$^2$ for the resist thickness of 1.1864 nm.

Eo is defined here as the minimum exposure dose required to completely dissolve the resist film in large unpatterned areas (greater than 10 microns).

The optimum exposure energy for the resist of Example 3 is 150 mJ/cm$^2$ at 0.99 micron of resist thickness. The resolution of this resist using 0.52 NA i-line stepper is 0.39 micron. The depth of focus for the resist was 0.9 microns for 0.5 micron line and space patterns. The profile was measured as 89 degrees.

It was unexpected that the addition of the compound would result in the development characteristics of this photoresist.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. The process of developing an image-wise exposed photoresist-coated substrate to form a positive-working image comprising:
   (a) coating said substrate with a radiation-sensitive composition useful as a photoresist, said composition comprising an admixture in a solvent of: at least one alkali-soluble binder resin, at least one o-quinonediazide photoactive compound, and an effective sensitive enhancing amount of at least one phenolic derivative of 4-(4-hydroxyphenol) cyclohexanone compound of formula (I):

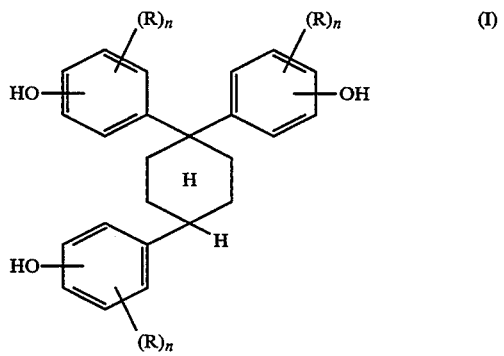

where each R is individually selected from the group consisting of hydrogen and a lower alkyl group having 1-4 carbon atoms and each n is 0, 1, or 2; the amount of said binder resin being about 60 to 95% by weight, the amount of said photoactive compound being about 5% to about 50% by weight, based on the total solids content of said radiation-sensitive composition;
   (b) subjecting said coating on said substrate to an image-wise exposure of radiant light energy; and
   (c) subjecting said image-wise exposed coated substrate to a developing solution to form a positive-working, image-wise pattern in the coating.

2. The process of claim 1 wherein said binder resin is an alkali-soluble phenolic novolak resin.

3. The process of claim 1 wherein said o-quinonediazide compound or compounds are present in the amount of about 10% to about 25% by weight, said binder resin is present in the amount of about 75% to about 90% by weight, and said phenolic derivative of 4-(4-hydroxyphenol) cyclohexanone is present in the amount of 0.5% to about 10% by weight, all based on the total solids content of said radiation-sensitive composition.

4. The process of claim 1 wherein said phenolic derivative of 4-(4-hydroxyphenol) cyclohexanone is present in the amount of from about 2% to about 4% by weight, based on the total solids content of said radiation-sensitive composition.

5. The process of claim 1 wherein said phenolic derivative of 4-(4-hydroxyphenol) cyclohexanone is 1,1,4-tris(4-hydroxyphenyl) cyclohexanone.

6. The process of claim 1 wherein said radiant light energy is selected from the group consisting of ultraviolet light radiation and electron beam radiation.

7. The process of claim 1 wherein said developing solution is an aqueous solution of an alkali selected from the group consisting of tetramethylammonium hydroxide, sodium hydroxide, potassium hydroxide, ethanolamine, choline, sodium phosphates, sodium carbonate, and sodium metasilicates.

* * * * *